US00PP28225P3

(12) United States Plant Patent
Kordes

(10) Patent No.: US PP28,225 P3
(45) Date of Patent: Aug. 1, 2017

(54) SHRUB ROSE PLANT NAMED 'KORWEDESI'

(50) Latin Name: *Rosa hybrida*
Varietal Denomination: KORwedesi

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 140 days.

(21) Appl. No.: 14/545,933

(22) Filed: Jul. 8, 2015

(65) Prior Publication Data

US 2016/0014938 P1 Jan. 14, 2016

Related U.S. Application Data

(60) Provisional application No. 61/998,919, filed on Jul. 11, 2014.

(51) Int. Cl.
*A01H 5/02* (2006.01)

(52) U.S. Cl.
USPC ..... Plt./107

(58) Field of Classification Search
USPC ..... Plt./101, 102, 107
See application file for complete search history.

(56) References Cited

PUBLICATIONS

Help Find Me: Roses, Clematis and Peonies website. Citation for Weg der Sinne; 'korwedesi'. https://www.helpmefind.com/rose/l.php?l=2.69541.0. Accessed Jan. 12, 2017. 1 page.*

* cited by examiner

*Primary Examiner* — Susan McCormick Ewoldt
*Assistant Examiner* — Karen Redden

(57) ABSTRACT

'KORwedesi' is a new and distinct variety of *Rosa hybrida* which is characterized by the combination of a bushy growth habit, medium-sized semi-double flowers which are violet-purple in color and also attractive foliage with excellent disease resistance. The new variety propagates successfully by grafting and by stem cuttings and has shown to be uniform and stable in the resulting generations from asexual propagation.

1 Drawing Sheet

Latin name of genus and species: The Latin name of the genus and species of the novel variety disclosed herein is *Rosa hybrida.*

Variety denomination The inventive variety of *Rosa hybrida* disclosed herein has been given the variety denomination 'KORwedesi'.

BACKGROUND OF THE INVENTION

The present invention relates to a new and distinct *Rosa hybrida*, shrub rose cultivar, which has been given the variety denomination of 'KORwedesi'. Its market class is PLT/102.

Parentage: The *Rosa hybrida* variety 'KORwedesi' is the result of a controlled cross-pollination breeding program carried out by the inventor in Offenseth-Sparrieshoop, Germany. The objective of the said breeding program was to create a new and distinct rose plant with unique qualities, such as:

1. Uniform growth and flowering;
2. Abundant attractive, recurrent purple-violet flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORwedesi' from all other varieties known to the inventor.

'KORwedesi' is a seedling selection which resulted from the controlled pollination of two proprietary *Rosa hybrida* breeding lines, developed and owned by the same inventor, during the summer of 2007. Said cross-pollination was made between an unnamed seedling, the seed parent, and another unnamed seedling, the pollen parent.

As part of a rose development program, Tim-Hermann Kordes germinated seeds from the aforementioned hybridization during the winter of 2007 and conducted evaluations and observations on the resulting seedlings in a controlled environment in Offenseth-Sparrieshoop, Germany. The resulting seedlings exhibited distinctive physical and biological characteristics. The new rose plant was selected as a single plant in May of 2008 from the seedling beds due to its superior characteristics and asexually propagated for further evaluation. This new and distinctive rose variety was given the name 'KORwedesi'.

Asexual Reproduction: The first asexual propagation of 'KORwedesi' was done by budding to seedling understocks in July of 2008 at the inventor's nursery in Offenseth-Sparrieshoop, Germany. These initial and other subsequent propagations conducted in controlled environments demonstrate that 'KORwedesi' reproduces true to type in successive generations of asexual reproduction.

SUMMARY OF THE INVENTION

The following characteristics have been repeatedly observed and represent the distinguishing characteristics of the new *Rosa hybrida* cultivar 'KORwedesi'. These traits, in combination, distinguish 'KORwedesi' as a new and distinct cultivar.

1. *Rosa hybrida* 'KORwedesi' exhibits a bushy growth habit; and
2. *Rosa hybrida* 'KORwedesi' exhibits a semi-double flower habit; and
3. *Rosa hybrida* 'KORwedesi' exhibits a medium flower size; and
4. *Rosa hybrida* 'KORwedesi' exhibits a purple-violet flower color, at anthesis; and
5. *Rosa hybrida* 'KORwedesi' exhibits medium green, matte foliage; and
6. *Rosa hybrida* 'KORwedesi' exhibits excellent disease resistance.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORwedesi', taken from plants of two years of age.

DETAILED BOTANICAL DESCRIPTION

The following is a detailed botanical description of a new and distinct variety of *Rosa hybrida* known as 'KORwedesi', based upon observations of plants of two years of age growing in June of 2015 at a nursery in Jackson County, Oreg.

Those skilled in the art will appreciate that certain characteristics will vary with older or, conversely, with younger plants. 'KORwedesi' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2001 edition except where common terms of color are used.

A botanical description of 'KORwedesi' and comparisons with other varieties of *Rosa hybrida* are provided below.

General plant description:

*Growth rate*.—Vigorous.

*Growth habit*.—Bushy and arching.

*Mature dimensions*.—Approximately 100 cm tall and 120 cm wide.

*Cold hardiness*.—To date, the variety has been grown successfully in USDA Hardiness Zone 5.

*Propagation*.—Grafting and stem cuttings.

*Disease resistance*.—Excellent resistance to powdery mildew (*Sphaerotheca pannosa*) and blackspot (*Diplocarpon rosae*) diseases under normal growing conditions in Jackson County, Oreg.

Root system:

*Type*.—Fibrous root system with many root hairs.

*Branching*.—Freely branched.

*Density*.—Moderately dense rooting.

*Distribution*.—Roots distributed uniformly throughout the soil profile, from shallow to deep.

*Color*.—Orange-white, nearest to RHS 159D.

Stems:

*Stem color*.—Immature stems are Yellow-Green Group 144A; mature stems are Yellow-Green Group 144B.

*Intonations*.—None observed.

*Stem surface texture*.—The surfaces of both immature and mature stems are smooth.

*Stem diameter*.—10 mm.

*Prickles*.—Incidence — Present; 10 prickles per 10 cm of stem, on average. Size — Average length is 12 mm. Immature prickle color — Yellow-Green Group 145C. Mature prickle color — Yellow-Green Group 145A. Anthocyanin — Greyed-Purple Group 184A. Shape — Deeply concave. Texture — Smooth.

Leaves:

*Arrangement*.—Imparipinnate compound leaves; mature axillary leaves consisting of 7 leaflets.

*Attachment*.—Petiolate.

*Dimensions*.—165 to 180 mm long and 120 to 135 mm wide.

*Abundance*.—Very abundant.

*Stipules*.—Size — 35 mm long and 10 mm wide. Stipule color — Yellow-Green Group 144A; Yellow-Green Group 145C at and near the midrib. Anthocyanin — Greyed-Purple Group 184A; present on stipitate glands. Stipitate glands — Abundant; only present at margins. Margins — Glandular toothed. Texture, adaxial surface — Leathery. Texture, adaxial surface — Glabrous. Apex — Apiculate. Base — Winged.

*Petiole*.—Length — Average 45 to 50 mm. Diameter — Average 2 mm. Petiole color, adaxial surface — Yellow-Green Group 145A. Petiole color, abaxial surface — Yellow-Green Group 145A. Margins — Glandular toothed. Anthocyanin — Greyed-Purple Group 184A on stipitate glands and prickles. Prickles — Typically one small prickle present on the abaxial surface. Stipitate glands — Limited number present on margins. Texture, adaxial surface — Papillate. Texture, abaxial surface — Glabrous. Strength — Moderate.

*Rachis*.—Length — Average 15 to 20 mm. Diameter — Average 1 to 2 mm. Color — Yellow-Green Group 145A. Anthocyanin — Greyed-Purple Group 182A, present on stipitate glands and prickles. Margins — Glandular toothed. Texture — Pappilate. Prickles — A few small prickles underneath. Stipitate glands — Limited numbers of stipitate glands on margins and abaxial surface.

*Leaflets*.—Quantity — Normally 7 leaflets on normal leaves in middle of the stem. Dimensions — Average size of the terminal leaflet is 65 to 70 mm long and 40 to 45 mm wide. Shape — Ovate. Apex — Acute. Base — Obtuse. Margins — Serrated. Texture, adaxial surface — Semi-glossy and smooth. Texture, abaxial surface — Matte and leathery. Juvenile foliage color, adaxial surface — Yellow-Green Group 146A. Juvenile foliage color, abaxial surface — Yellow-Green Group 146B. Mature foliage color, abaxial surface — Green Group 137A. Mature foliage color, abaxial surface — Yellow-green Group 146B. Anthocyanin intonation — Greyed-Purple Group 184A. Present on margins and abaxial surface of juvenile foliage. Venation — Reticulate. Petiolule — Dimensions — 3 to 4 mm long and 1 mm in diameter. Petiolule color, adaxial surface — Yellow-Green Group 145A. Petiolule color, abaxial surface — Yellow-Green Group 145A. Prickles — Few small prickles are present on the abaxial surface. Texture, adaxial surface — Smooth, with a few stipitate glands present. Texture, adaxial surface — Smooth, with a few stipitate glands present. Margins — Stipitate glands present along margins.

Inflorescence:

*Inflorescence type*.—Corymb with flowers held upright.

*Blooming habit*.—Recurrent and floriferous.

*Quantity of flowers*.—7 to 10, on average.

*Size*.—90 mm tall and 140 mm wide, on average.

*Peduncle*.—Surface — Limited numbers of fine hairs and stipitate glands with an abundance of small prickles present. Length — 35 to 85 mm average length. Diameter — 3.5 to 4.0 mm average diameter. Color — Yellow-Green Group 144A. Anthocyanin — Intonations of Greyed-Red Group 182A on prickles only. Texture — Hispid. Strength — Strong.

Flowering laterals: Present below the initiation of inflorescence. Generally 5 flowering laterals are present, with 35 to 50 flowers each.

Bud:

*Bud form*.—Long. Pointed ovoid.

*Size*.—Upon opening, 20 to 25 mm in length from base of receptacle to distal end of bud and 13 mm diameter at its widest point.

*Texture*.—Smooth.

*Color, as sepals first unfold*.—Red-Purple Group 58A.

*Color when one-quarter open, inner surface*.—Marginal zone — Red-Purple Group 61B. Middle zone — Red-Purple Group 61B with intonations of Yellow Group 9B. Basal zone — Yellow Group 9B.

*Color when one-quarter open, lower surface of petal*.—Marginal zone — Red-Purple Group 61B. Middle zone — Yellow Group 9C with intonations of Red-Purple 61B. Basal zone — Yellow Group 9C.

Flower:

Pedicel:

*Surface*.—Pubescent with abundant stipitate glands present.

*Length*.—30 to 40 mm, on average.

*Diameter*.—1.5 to 2.5 mm, on average.

*Color*.—Yellow-Green Group 145A.

*Intonations*.—Greyed-Red Group 182A on stipitate glands only.

*Strength*.—Strong.

*Texture*.—Hispid.

Sepals:

*Diameter of calyx*.—12 to 25 mm at anthesis.

*Color, adaxial surface*.—Greyed-Green Group 194A.

*Color, abaxial surface*.—Yellow-Green Group 146B.

*Intonations*.—Greyed-Purple 184B on stipitate glands and occasionally on the midrib.

*Size*.—25 mm long and 6 to 7 mm wide, on average.

*Shape*.—Weak foliaceous appendages on 1 to 3 of the 5 sepals.

*Apex*.—Apiculate.

*Base*.—Flat at union with receptacle.

*Quantity*.—Five.

*Texture, adaxial surface*.—Hoary.

*Texture, abaxial surface*.—Smooth with fine white hairs.

*Margins*.—Cilliate and glandular toothed observed.

*Stipitate glands*.—Abundant along margins.

Corolla:

*Corolla habit*.—Semi-double.

*General shape of corolla*.—Cup-open; shallow; round.

*Shape of corolla when viewed from the side*.—Upon opening, upper portion — Flattened convex. Upon opening, lower portion — Flattened convex. Open flower, upper portion — Flat. Open flower, lower portion — Concave.

*Aspect*.—Flowers held upright.

*Dimensions*.—Medium for a shrub rose. When open, the average flower diameter is 60 to 75 mm and the average flower height is 15 mm.

*Fragrance*.—Light.

*Duration*.—On the plant 3 to 4 days. Senesced petals drop away.

*Petals*.—Petal Arrangement — Not formal. Petal Count — Approximately 7 to 8 petals under normal conditions. Petal Reflex — Petals are slightly reflexed. Reflex occurs simultaneously. Petal Margin — Erose to incised, typically with 1 to 3 incisions. Petal Shape — Obcordate. Apex — Retuse. Base — Obtuse. Dimensions — Approximately 25 to 32 mm long and 25 to 36 mm wide. Texture, inner surface — Smooth. Texture, outer surface — Smooth. Petal color, upon opening — Outermost petals, outer surface — Marginal zone — Red-Purple Group 61B. Middle zone — Yellow Group 9C with intonations of Red-Purple Group 61B. Basal zone — Yellow Group 9C. Outermost petals, inner surface — Marginal zone — Red-Purple Group 61B. Middle zone — Red-Purple Group 61B with intonations of Yellow Group 9B. Basal zone — Yellow Group 9B. Innermost petals — Upon opening, both the inner and outer surfaces of the innermost petals exhibit the same colorations as the inner and outer surfaces of the outermost petals. Basal petal spots, upon opening — Basal petal spot, outermost petals — Dimensions — 2 mm high and 2 mm wide. Color, outer surface — Green-Yellow Group 1B. Color, inner surface — Yellow Group 6B. Basal petal spot, innermost petals — Dimensions — 2 mm high and 2 mm wide. Outer surface — Yellow Group 2A. Inner surface — Yellow Group 2B. Petal color, after opening — Outermost petals, outer surface — Marginal zone — Red-Purple Group 61B. Middle zone — Red-Purple Group 63A. Basal zone — Yellow Group 9C. Outermost petals, inner surface — Marginal zone — Red-Purple Group 61B. Middle zone — Red-Purple Group 61B. Basal zone — Yellow Group 9B. Innermost petals, outer surface — Marginal zone — Red-Purple Group 63B. Middle zone — Red-Purple Group 63B. Basal zone — Yellow Group 9C. Innermost petals, inner surface — Marginal zone — Red-Purple Group 61B. Middle zone — Red-Purple Group 61B. Basal zone — Yellow Group 9B. Basal petal spots, after opening — Basal petal spot, outermost petals — Dimensions — 3 mm high and 3 mm wide. Color, outer surface — Yellow Group 2B. Color, inner surface — Yellow Group 2B. Basal petal spot, innermost petals — Dimensions — 2 mm high and 2 mm wide. Outer surface — Green-Yellow Group 1C. Inner surface — Yellow Group 2C. General Tonality — On open flower Red-Purple Group 61B. No change in the general tonality at the end of the 4th day. Afterwards, general tonality is Red-Purple N74B.

*Petaloids*.—Quantity — 4 petaloids per flower, on average. Dimensions — Approximately 12 to 25 mm long and 3 to 15 mm wide. Color, inner surface — Marginal zone — Red-Purple Group 61B. Middle zone — Red-Purple Group 61B. Basal zone — Yellow Group 9B. Color, outer surface — Marginal zone — Red-Purple Group 63A. Middle zone — Red-Purple Group 63A with intonations of Yellow Group 9C. Basal zone — Yellow Group 9C. Texture, inner surface — Smooth. Texture, outer surface — Smooth. Margins — Undulated; indented. Shape — Generally cuneate; some petaloids are highly irregular. Apex — Obtuse. Base — Cuneate.

Reproductive organs:

Stamens:

*Quantity*.—Approximately 110, on average, and regularly arranged around the styles.

*Anthers*.—Shape — Reniform. Dimensions — 2.0 mm long and 1.5 mm wide, on average. Color — Yellow Group 10B. Pollen — Generally present; medium density. Pollen Color — Greyed-Orange Group N163D.

*Filaments*.—Color — Yellow-Orange Group 16B with intonations of Greyed-Orange Group 166B. Length — 5 to 10 mm.

Pistils:

*Quantity*.—Few; approximately 25 to 50 present.

*Stigmas*.—Dimensions — 1 mm long and 1 mm wide. Location — Level with or slightly inferior to anthers. Color — Greyed-Yellow Group 162A.

*Styles*.—Length — Approximately 5 mm long. Color — Red-Purple Group N57C.

Ovary:

*Dimensions*.—2 mm long and 1 mm in diameter.

*Color*.—Green-White 157A.

Receptacle:

*Shape*.—Pear-shaped.

*Dimensions*.—Approximately 7 mm high and 6 mm wide.

*Surface*.—Slightly glaucous, with a limited number of fine hairs present.

*Color*.—Yellow-Green Group 144A.

*Texture*.—Smooth.

Hips and seed formation: Not observed to date.

COMPARISONS WITH THE PARENTS

The new rose plant may be distinguished from its seed parent, an unnamed seedling, by the following combination of characteristics:

1. 'KORwedesi' exhibits a violet-purple flower color, whereas the unnamed seedling exhibits a pink flower color.
2. 'KORwedesi' exhibits a semi-double corolla habit, whereas the unnamed seedling exhibits a single corolla habit.

The new rose plant may be distinguished from its pollen parent, an unnamed seedling, by the following combination of characteristics:

1. 'KORwedesi' exhibits excellent disease resistance, whereas the unnamed seedling exhibits average disease resistance.
2. 'KORwedesi' exhibits a bushy and arching growth habit, whereas the unnamed seedling exhibits an upright growth habit.

COMPARISONS WITH SIMILAR *ROSA HYBRIDA* CULTIVARS KNOWN TO THE INVENTOR

For a comparison, several physical characteristics of the rose variety 'KORdwarul', a rose variety from the same inventor described and illustrated in U.S. Plant Pat. No. 19,746 and filed on Aug. 15, 2007, are compared to 'KORwedesi' in Chart 1.

CHART 1

| Characteristic | 'KORwedesi' | 'KORdwarul' |
|---|---|---|
| Average plant height and width. | 100 cm high and 120 cm wide. | 60 cm high and 60 cm wide. |
| Open flower diameter. | 60 to 75 mm. | 30 mm. |
| Basal petal spots on the outer surface of the outermost petals, upon opening of flower | Green-Yellow Group 1B. | Yellow Group 1D to White Group 57A. |

That which is claimed:

1. A new and distinct variety of rose plant named 'KORwedesi', as described and illustrated herein.

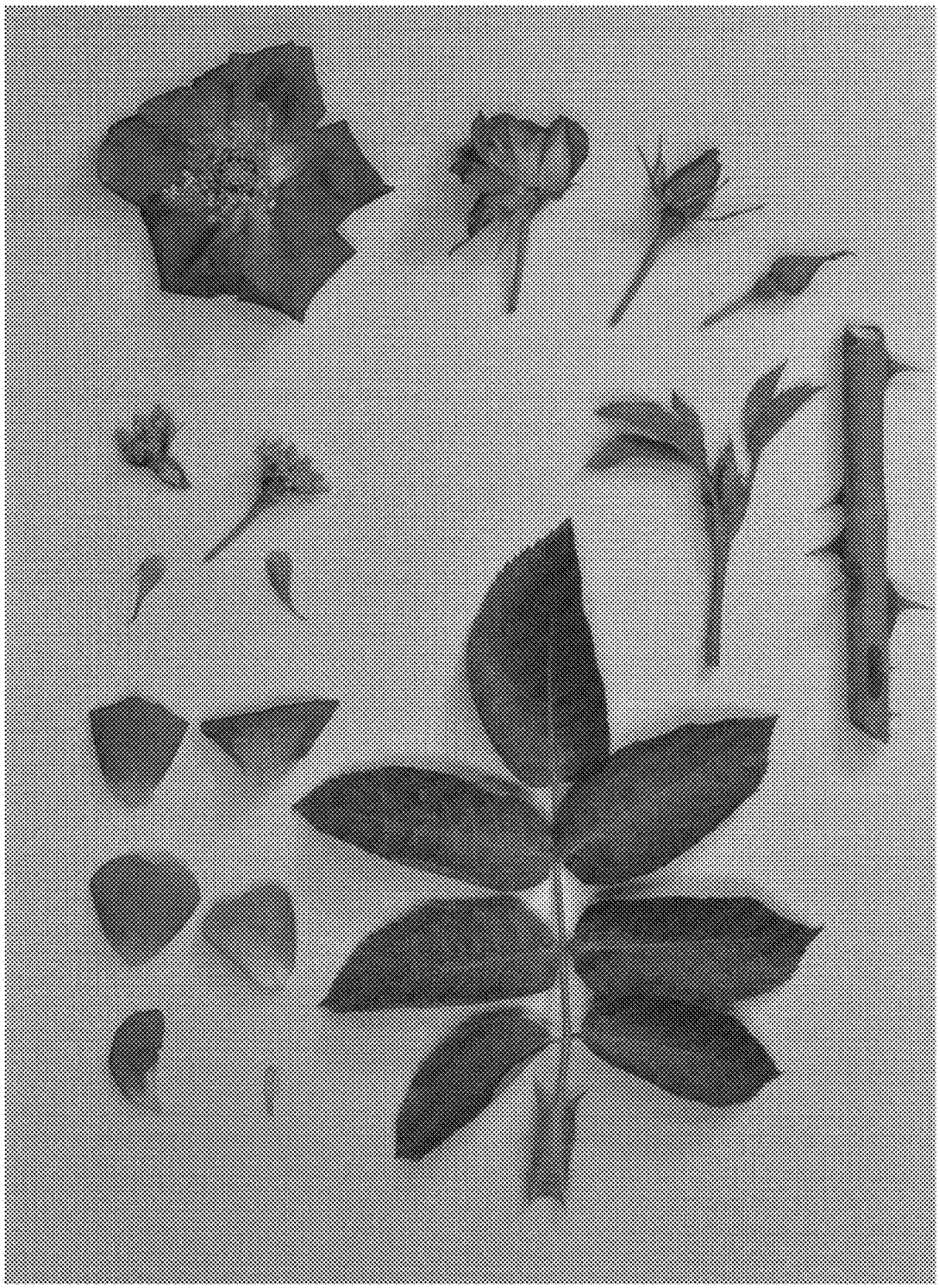

* * * * *